United States Patent [19]

Popovich

[11] Patent Number: 5,602,929
[45] Date of Patent: Feb. 11, 1997

[54] FAST ADAPTING CONTROL SYSTEM AND METHOD

[75] Inventor: Steven R. Popovich, Stoughton, Wis.

[73] Assignee: Digisonix, Inc., Middleton, Wis.

[21] Appl. No.: 380,343

[22] Filed: Jan. 30, 1995

[51] Int. Cl.⁶ .............................. A61F 11/06; H03B 29/00

[52] U.S. Cl. ........................................ 381/71; 364/724.19

[58] Field of Search .................. 381/71, 94; 364/724.19; 267/140.14, 140.15; 188/299; 181/206

[56] References Cited

U.S. PATENT DOCUMENTS

| | | |
|---|---|---|
| 4,677,676 | 6/1987 | Eriksson . |
| 4,677,677 | 6/1987 | Eriksson . |
| 4,987,598 | 1/1991 | Eriksson ................................... 381/71 |
| 5,251,262 | 10/1993 | Suzuki et al. ............................. 381/71 |
| 5,278,913 | 1/1994 | Delfosse et al. .......................... 381/71 |
| 5,337,366 | 8/1994 | Eguchi et al. ............................. 381/71 |
| 5,390,255 | 2/1995 | Popovich .................................. 381/71 |
| 5,396,561 | 3/1995 | Popovich et al. ......................... 381/71 |
| 5,418,857 | 5/1995 | Eatwell .................................... 381/71 |

OTHER PUBLICATIONS

"Constraint filtered-x and filtered-u least-mean-square algorithms for the active control of noise in ducts", by Kim et al, J.Acoust.Soc.Am. 95(6), Jun. 1994, pp. 3379–3389.

Kim, In-Soo et al, "Constraint Filtered-x and Filtered-u Least-mean-square Algorithms for the Active control of Noise in Ducts", L. Acoust. Soc. Am., 95(6), Jun. 1994, pp. 3379–3389. Jun. 1994.

Active Noise Cancellation using a Modified Form of the Filtered-X LMS Algorithm, Bjarnason, Signal Processing VI Theories and Applications, Proceedings of EUSIPCO–92, Sixth European Signal Processing Conference, Brussels, Belgium, Aug. 24–27, 1992, vol. II.

*Primary Examiner*—Curtis Kuntz
*Assistant Examiner*—Ping W. Lee
*Attorney, Agent, or Firm*—Andrus, Sceales, Starke & Sawall

[57] ABSTRACT

An active control system having an adaptive filter model in which the effect of transfer functions after the adaptive filter model output are eliminated from the adaption process. The adaptive control scheme inputs a reference signal to a copy of the adaptive filter model, and the copy of the adaptive filter model outputs a correction signal that drives an output transducer. The copy of the adaptive filter model does not receive an error input signal. Adaption occurs in the adaptive filter model. The model input to the adaptive filter model is a C-filtered reference signal. There are no transfer functions between the output of the adaptive filter model and the error input to the adaptive filter model. The error input to the adaptive filter model is a combination of an error signal from an error sensor, a C-filtered correction signal, and a model output signal from the adaptive filter model.

13 Claims, 7 Drawing Sheets ss
5,602,929

FAST ADAPTING CONTROL SYSTEM AND METHOD

BACKGROUND

The invention is a fast adapting control system and method that is particularly useful for tracking in an active acoustic attenuation system.

Active acoustic attenuation involves injecting a canceling acoustic wave to destructively interfere with and cancel a system input acoustic wave to yield a system output acoustic wave. In an active acoustic attenuation system, an adaptive control filter receives a reference signal and in turn supplies a correction signal to an output transducer such as a loudspeaker in a sound application or a shaker in a vibration application. The output transducer injects the canceling acoustic wave or secondary input to destructively interfere with the system input so that the system output is zero or some other desired value.

The system output acoustic wave is sensed with an error sensor such as a microphone in a sound system, or an accelerometer in a vibration system. The error sensor generates an error signal in response to the system output. An error input signal, which depends at least in part on the error signal, is supplied to the adaptive control filter, and adaptive parameters in the control filter are updated in relation to the error input signal to adapt the filter. A convergence factor or step size parameter $\mu$ is normally selected to ensure convergence of the adaptive control filter.

It is important that the adaptive control filter in an active acoustic attenuation system be stable (i.e. converge), and also that the adaptive filter be robust. One consideration in this respect, is that the adaptive control filter account for propagation delay and phase shifts in an auxiliary path between the output of the adaptive control filter and the output of the error sensor. The filtered-X least-means-square (LMS) and the filtered-U recursive-least-means-square (RLMS) update methods as described in U.S. Pat. No. 4,677,676 which is incorporated herein by reference, account for the delay and phase shifts in the auxiliary path when updating the adaptive control filter model, and are effective means of providing adaptive control in many active acoustic attenuation systems. In the filtered-X and filtered-U methods, it is normally preferred that C modeling of the auxiliary path be accomplished adaptively on-line such as described in above incorporated U.S. Pat. No. 4,677,676. Other methods such as delayed inverse C modeling, or delayed Hermetian transpose C modeling can also be used to account for delay and phase shift in the auxiliary path.

Even if these methods are used, propagation delay in the auxiliary path can cause some instability in the adaptive control filter model if the convergence factor or step size $\mu$ is too large.

SUMMARY OF THE INVENTION

The invention provides a method of adapting an adaptive control system in which the effect of propagation delay through the auxiliary path is eliminated from the adaptation process. The maximum stable step size $\mu$ can therefore be increased, and the adaptive filter control model can thus be more robust.

The invention can be embodied in an adaptive controller having an adaptive filter model with an error input, and no transfer functions experiencing propagation delay or phase shifts between the output of the adaptive filter model and the error input to the adaptive filter model. This adaptive control scheme is implemented by using a copy of the adaptive filter model that inputs a reference signal, and outputs a correction signal that drives the output transducer. The correction signal also inputs a correction signal filter which is preferably a copy of a C model to generate a filtered correction signal. The filtered correction signal is combined with an error signal from an error sensor to generate an uncanceled equation error signal which is an estimate of what the system output would be in the absence of a secondary input into the system from the output transducer. This uncanceled equation error signal can be combined with a model output signal from the adaptive filter model to generate a model error signal that is used to adapt the adaptive filter model.

A copy of the C model is preferably provided before the adaptive filter model, rather than after the adaptive filter model. This is possible because both the C model and the adaptive filter model are slowly adapting. The adaptive filter model can therefore adapt without consideration of propagation delay or phase shifts due to transfer functions in the auxiliary path between the output of the adaptive filter model and the error input to the adaptive filter model.

The invention can be implemented in a feedforward system, or a feedback system. The invention can also be implemented in a multiple input, multiple output, and multiple error (MIMO) system.

While the invention is useful for active acoustic attenuation such as sound or vibration attenuation, the invention is also useful for other adaptive control applications in which there are transfer functions in the auxiliary path.

BRIEF DESCRIPTION OF THE DRAWINGS

Prior Art

Present Invention

Figure 3:
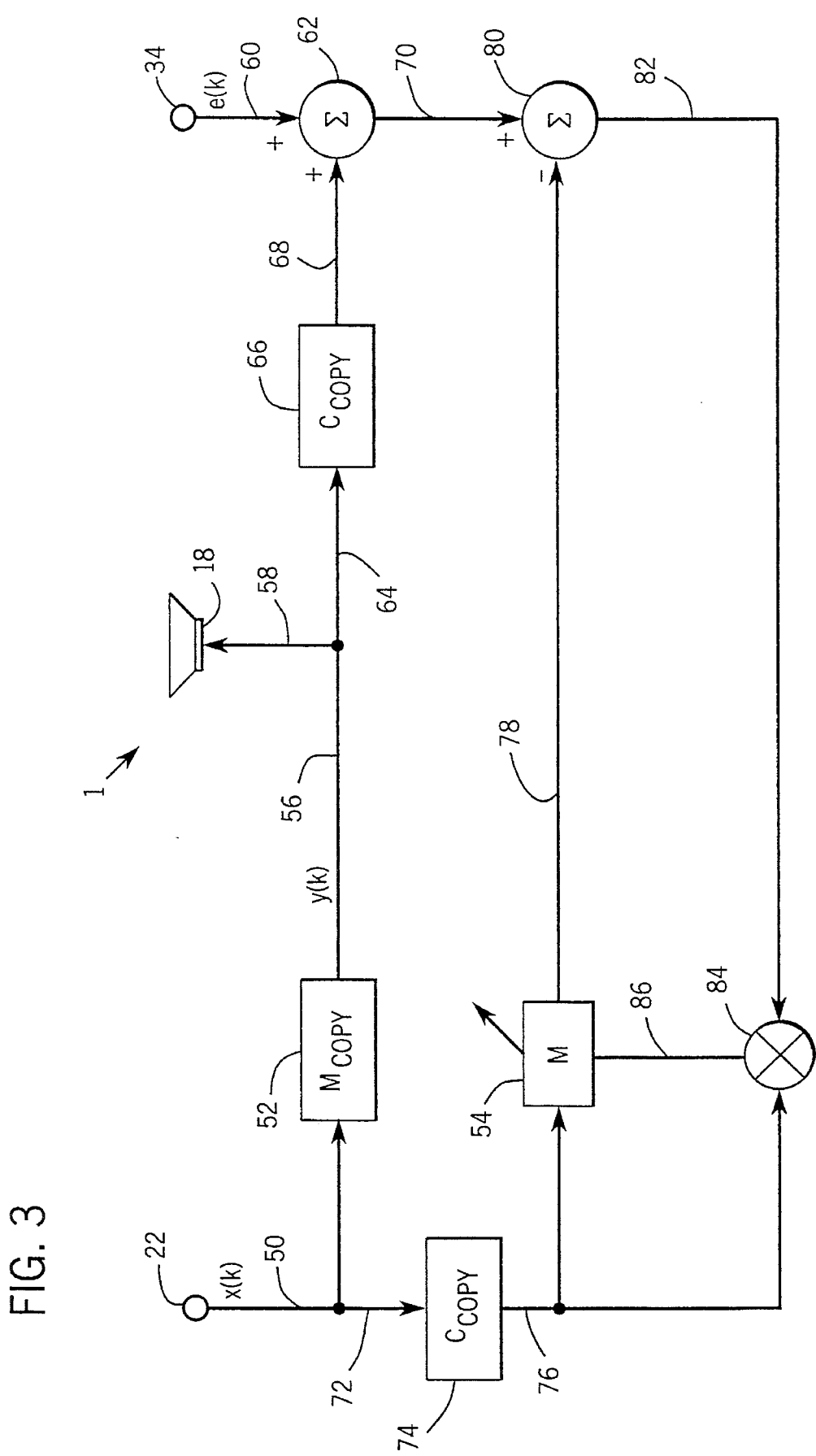

FIG. 3 is a schematic illustration of a feedforward adaptive control system in accordance with the invention.

Figure 4:
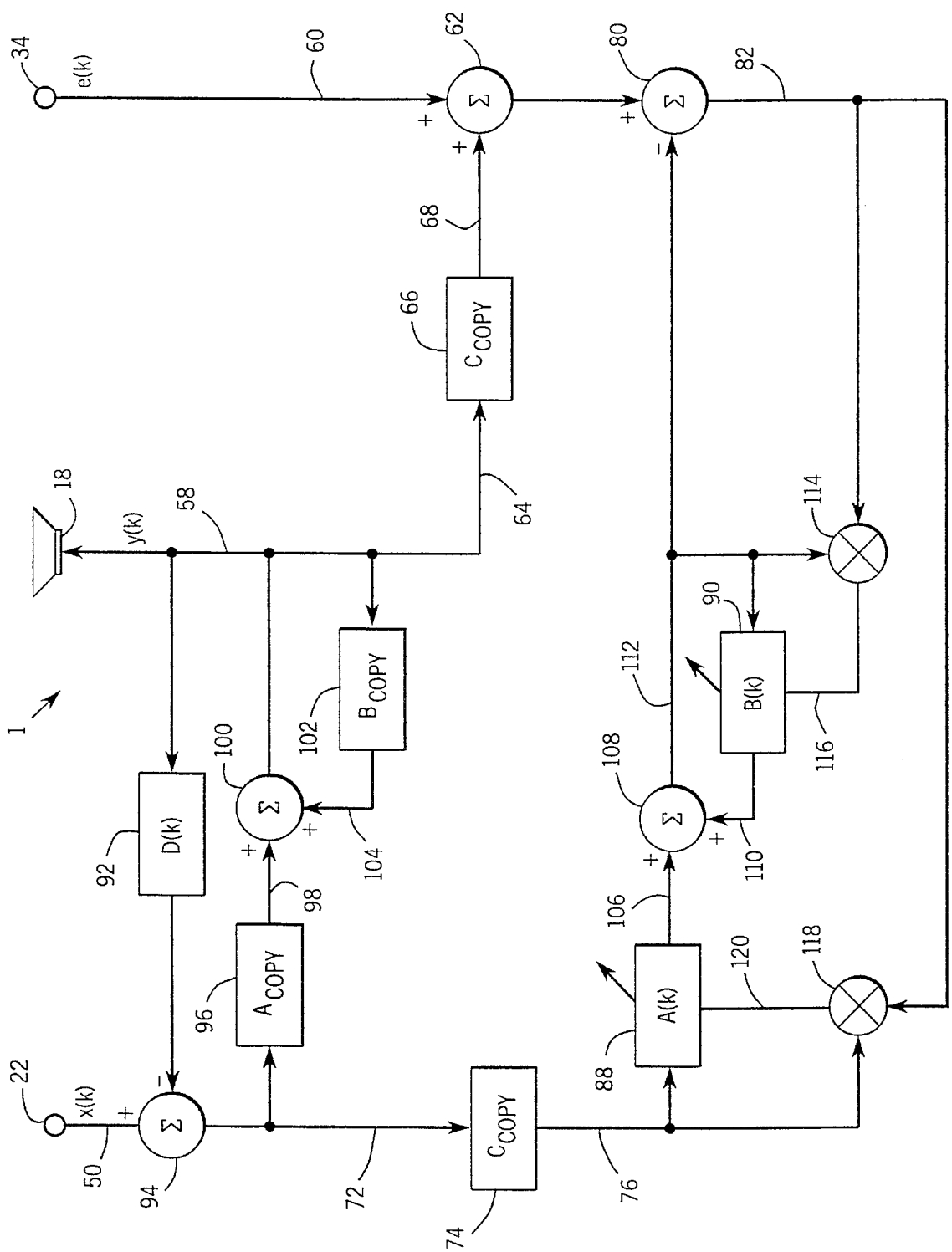

FIG. 4 is a schematic illustration showing a preferred embodiment of the system shown in FIG. 3.

Figure 5:
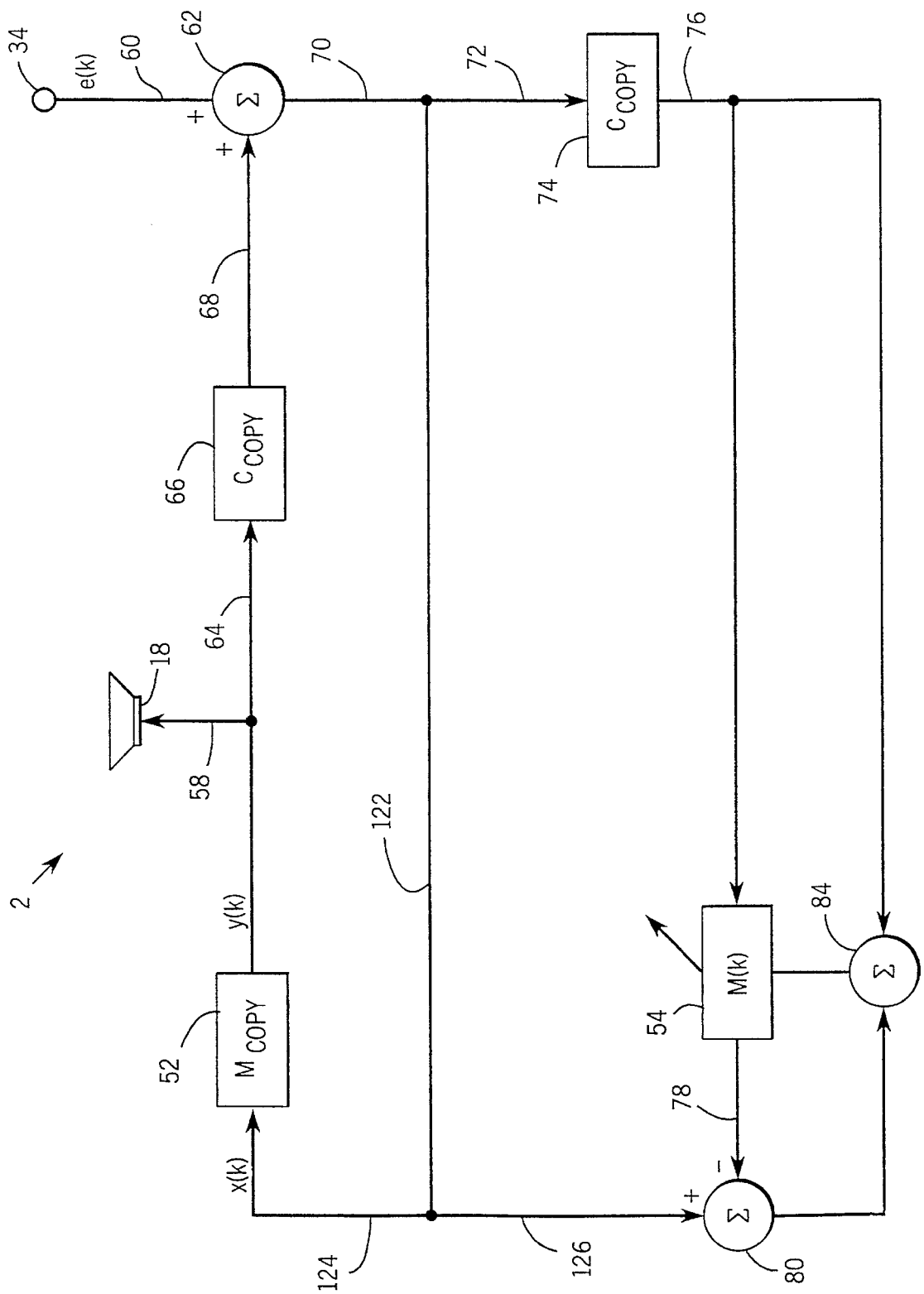

FIG. 5 is a schematic illustration of a feedback adaptive control system in accordance with the invention.

Figure 6:
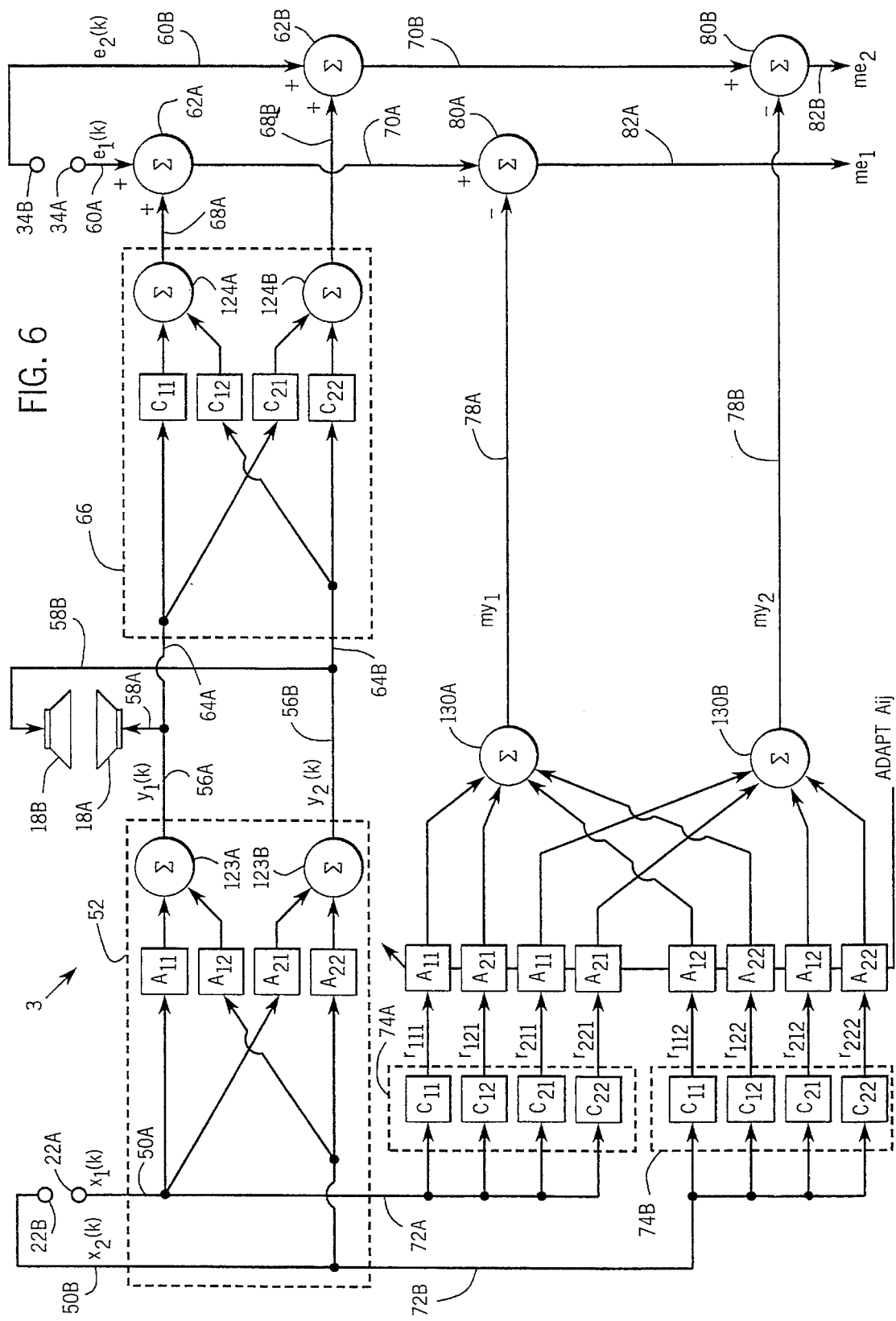

FIG. 6 is a schematic illustration showing a feed forward multiple input, multiple output, multiple error system in accordance with the invention.

Figure 7:
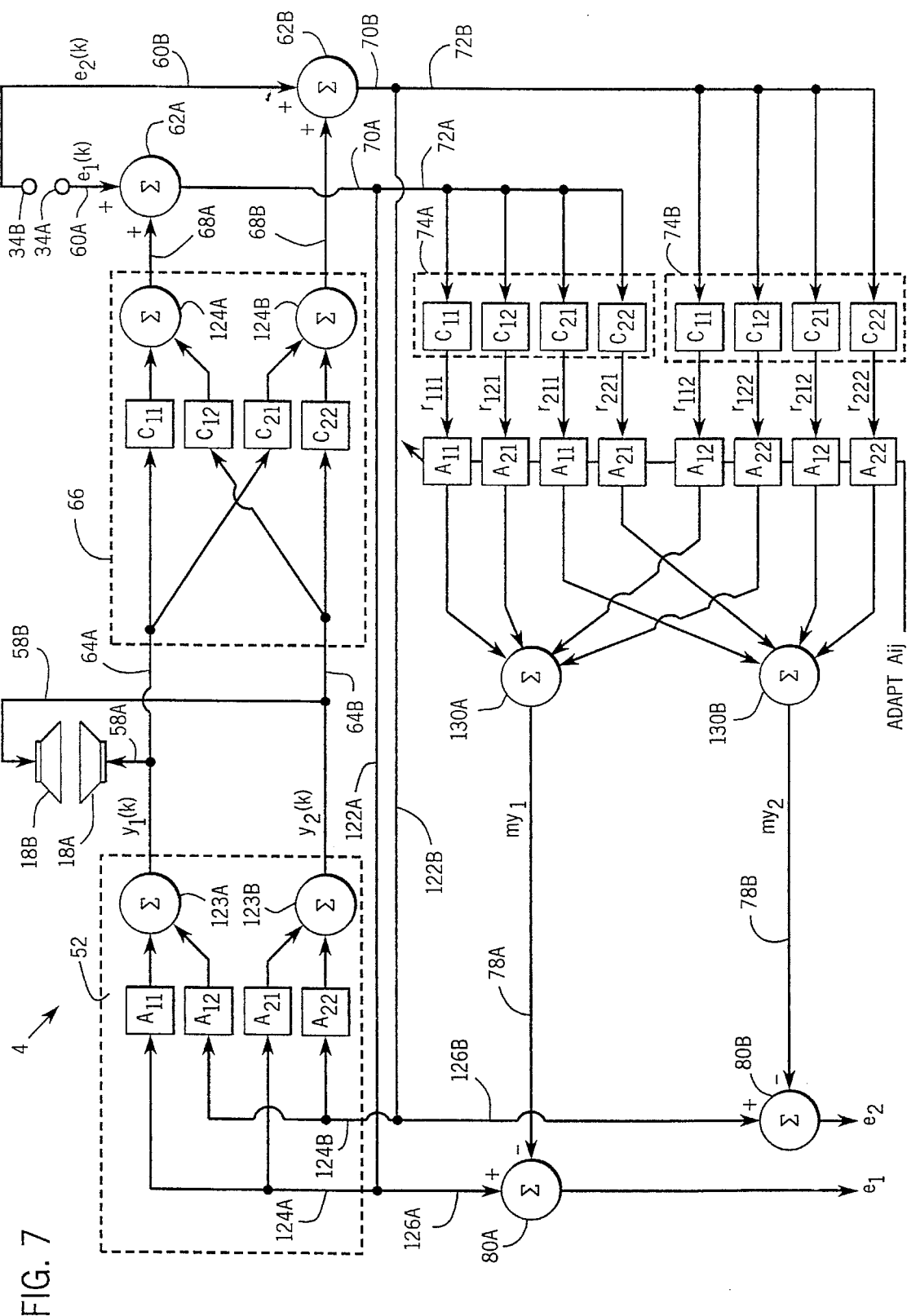

FIG. 7 is a schematic illustration showing a feedback multiple input, multiple output, multiple error system in accordance with the invention.

DETAILED DESCRIPTION

Prior Art

Figure 1:
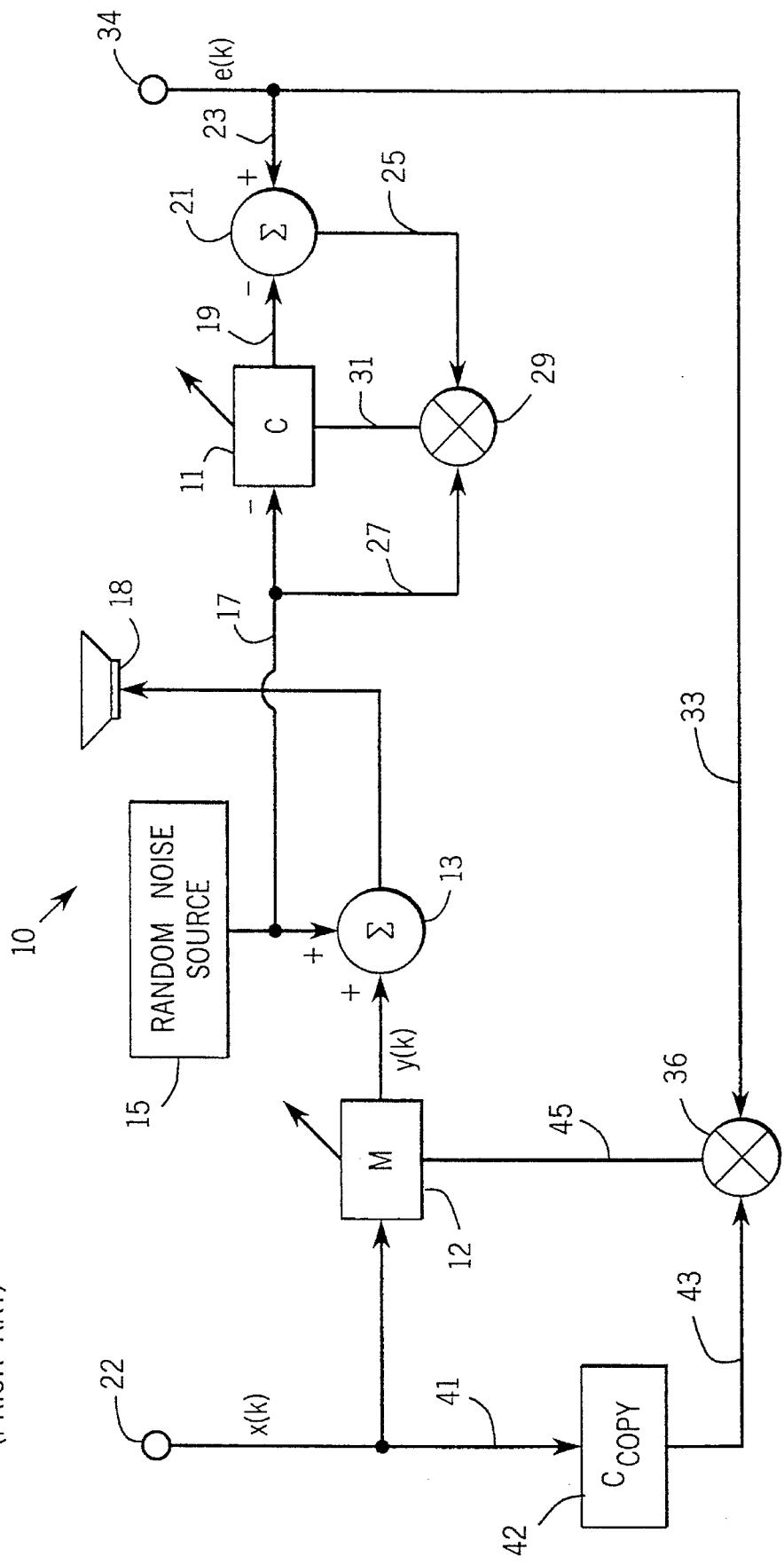
FIG. 1 is a schematic illustration of an adaptive control system implementing a filtered-X LMS update as is known in the art.

FIG. 1 shows an active acoustic attenuation system 10 with a feedforward adaptive control system implementing a filtered-X LMS update in the time domain. In the system 10 shown in FIG. 1, an input sensor 22 generates a reference signal x(k) that is processed in an adaptive M filter 12 to generate a correction signal y(k). The correction signal y(k)

is transmitted to a summing junction 13 where it is summed with low level random noise from a random noise source 15. The correction signal y(k) from the summing junction 13 is then transmitted to an output transducer 18. The output transducer 18 outputs a secondary input (i.e., a canceling acoustic wave) that combines with the system input (i.e., an input acoustic wave) to yield the system output (i.e., an output acoustic wave). An error sensor 34 senses the system output and generates an error signal e(k) in response thereto.

An auxiliary path between the output of the adaptive M filter 12 and the output of the error sensor 34 is modeled on line by C model 11. Low level random noise from random noise source 15 is transmitted in line 17 to C model 11, which outputs a signal in line 19. Summer 21 subtracts the signal in line 19 from the error signal in line 23, and outputs a signal in line 25. The signal in line 25 is transmitted to multiplier 29 where it is multiplied with low level random noise in line 27. The multiplier 29 outputs an error input signal 31 which is transmitted to C model 11 to update the adaptive parameters in the C model 11.

The reference signal x(k) is filtered through a copy 42 of the C model 11, and the resultant filtered-X reference signal is transmitted through line 43 to multiplier 36. The error signal e(k) is also transmitted to multiplier 36 through line 33. The multiplier outputs an error input signal in line 45 to the adaptive M filter 12.

In the above acoustic attenuation system 10 shown in FIG. 1, the adaptive M filter 12 is typically a transversal finite impulse response (FIR) filter. However, as described in incorporated U.S. Pat. Nos. 4,677,676, and 4,677,677 which is also incorporated by reference, the adaptive M filter 12 can be an infinite impulse response (IIR) filter. If the adaptive M filter 12 is an IIR filter, the filtered-U recursive-least-means-square (RLMS) update method should be used as disclosed in U.S. Pat. No. 4,677,676. The filtered-X or filtered-U update methods can be implemented in a feedforward system as shown in FIG. 1, or in a feedback system. In a feedback system, the error signal e(k) or a derivation thereof, can be used as the reference signal x(k).

Figure 2:
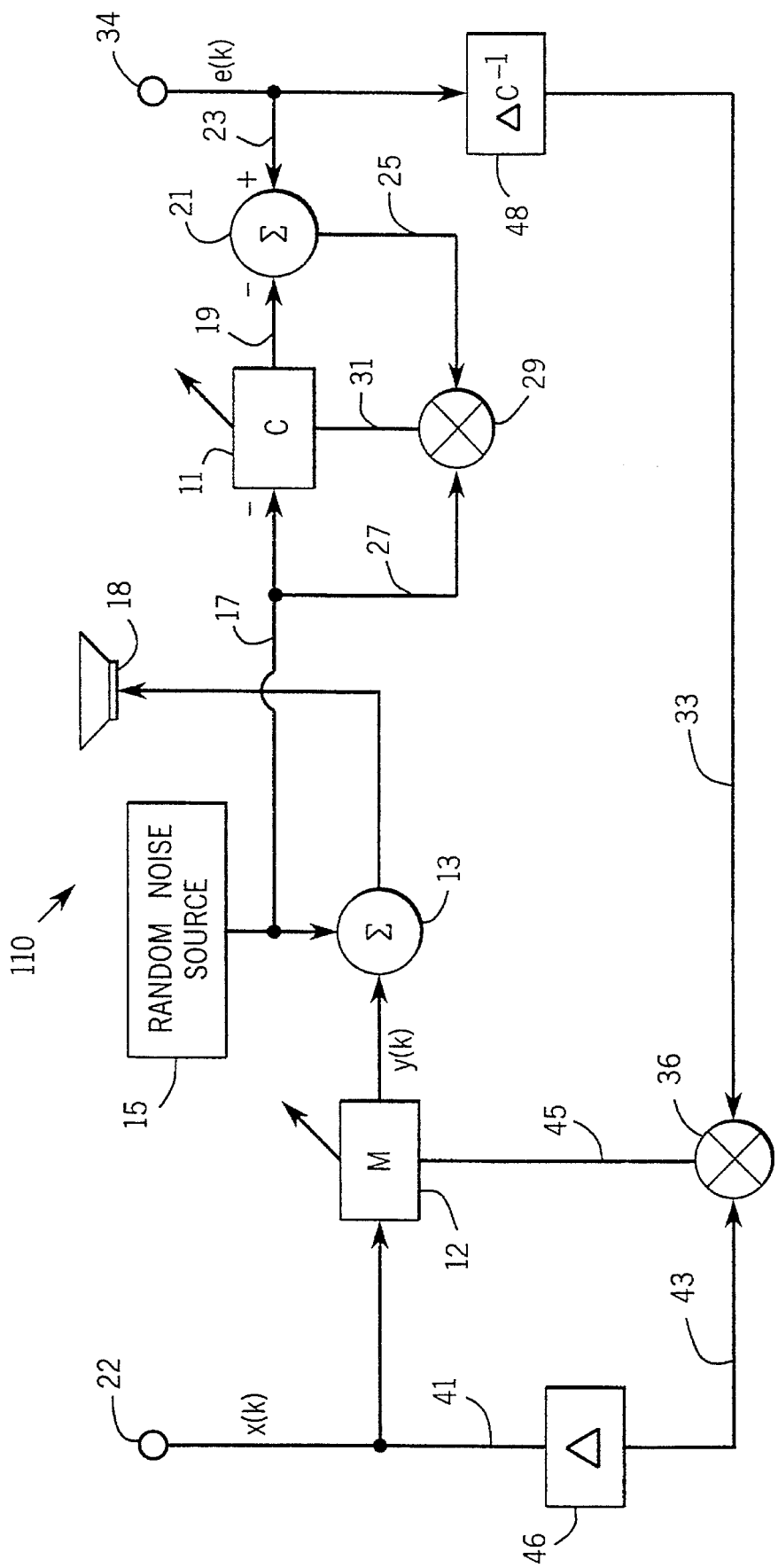
FIG. 2 is a schematic illustration of an adaptive control system implementing an LMS update with delayed inverse C modeling as is known in the art.

FIG. 2 shows another feedforward system 110 implementing the LMS or RLMS update method for active acoustic attenuation. The system 110 in FIG. 2 is an inverse C model system 110 as is also described in U.S. Pat. No. 4,677,676. The system 110 in FIG. 2 is similar in many respects to the filtered-X system shown in FIG. 1, and like reference numbers are used where appropriate to facilitate understanding.

In FIG. 2, a delay element 46 replaces the copy 42 of the C model 11 shown in FIG. 1. Also, a delayed inverse C model filter 48 is added in FIG. 2 to filter the error signal e(k). Depending on the application, it may be quite burdensome or even impossible to process a C model inverse on-line. Under many circumstances it may be preferred to implement a delayed Hermetian transpose C model in place of a delayed inverse C model 48, as disclosed in copending patent application entitled "Adaptive Control System with a Corrected Phase Filter Error Update", U.S. Ser. No. 08/297, 241 by Steven R. Popovich.

The systems 10 and 110 shown in FIGS. 1 and 2 correlate a delayed or filtered reference signal x(k), normally called a regressor, with the error signal e(k) or a filtered version thereof, to account for delay and phase changes in the auxiliary path so that the adaptive M filter 12 converges. A convergence factor or step size µ is multiplied times the error input signal in line 45 before adapting the adaptive weights in the M filter 12 to ensure convergence.

Present Invention

FIGS. 3–7 show the invention which is a fast adapting control system. The invention is particularly useful for tracking in an active acoustic attenuation system, however the invention may be used in other control system applications.

Referring to FIG. 3, the invention is shown in conjunction with a feedforward active sound attenuation system 1. An input microphone 22 senses a system input such as an input acoustic wave, and generates a reference signal x(k) in line 50. The reference signal x(k) in line 50 is transmitted to a copy 52 of an adaptive M filter model 54. The reference signal x(k) is processed by the copy 52 of the M filter model 54 to generate a correction signal y(k) in line 56. The correction signal y(k) is transmitted through line 58 to drive an output transducer 18.

The output transducer 18 outputs a secondary input that combines with the system input to yield the system output. The secondary input in this active sound attenuation system can be called a canceling acoustic wave. In non-acoustic control applications, the secondary input is analogous to a control signal.

The system output is sensed by an error microphone 34 which generates an error signal e(k). The error signal e(k) is transmitted in line 60 to an uncanceled equation error summer 62. The correction signal y(k) is not only transmitted to the output transducer 18, but is also transmitted through line 64 to input a C model copy 66. The correction signal y(k) in line 64 is filtered through the C model copy 66, and C model copy 66 outputs a filtered correction signal in line 68. The filtered correction signal in line 68 is summed in summing junction 62 with the error signal e(k) in line 60 to yield an uncanceled equation error signal in line 70. It is preferred that the C model copy 66 be a copy of an adaptive on-line C model as described in above incorporated U.S. Pat. No. 4,677,676. The C model should model the transfer function between the output of the copy 52 of the adaptive M filter model 54 and the error sensor 34, which is referred to herein as the auxiliary path. The uncanceled error equation signal in line 70 is thus an estimate of what the system output would be if no secondary input from the output transducer 18 were injected into the system 1.

The reference signal x(k) is not only transmitted to the copy 52 of the adaptive M filter model 54, but is also transmitted in line 72 to a reference signal filter 74 which is also preferably C model copy. The C model copy reference signal filter 74 is preferably a copy of the same C model or the C model copy correction signal filter 66. The C model copy 74 outputs a filtered reference signal in line 76. The adaptive M filter model 54 inputs the filtered reference signal and outputs a model output signal in line 78. The model output signal in line 78 is subtracted from the uncanceled equation error signal in line 70 in summer 80 to yield a model error signal in line 82. The filtered reference signal in line 76 is also transmitted to a multiplier 84. The model error signal in line 82 is input to the multiplier 84 where it is multiplied by the filtered reference signal to yield an error input signal in line 86. The error input signal in line 86 is input to the adaptive M filter model 54 to adapt the model 54. It can be appreciated that the model error signal in line 82 is an estimate of the error signal e(k) in line 60. This is because both are adaptive M filter model 54 and the C model copy reference signal filter 74 are in general slowly adapting. Since there are no transfer functions in the path from the output of the adaptive M filter model 54 until the generation of the model error signal in line 82, there is no need to account for propagation delay or phase shifts in auxiliary path during adaptation of M filter model 54. In some systems, this may allow the use of a larger step size μ without risking instability.

The adaptive M filter model 54 in system 1 of FIG. 3 can have various forms. For instance, the M filter 54 can be a direct FIR filter. Another embodiment of the invention with an IIR filter is shown in FIG. 4. The system 1 in FIG. 4 has three adaptive filters: a direct FIR A filter model 88, a recursive FIR B filter model 90, and a recursive D filter model 92. The adaptive D model 92 inputs the correction signal y(k) and outputs a D model output signal that is subtracted from an input signal from the input microphone 22 in summer 94 to yield reference signal x(k). The adaptive D model can be adapted on-line using a random noise technique similar to that for adaptive on-line C modeling as described in U.S. Pat. No. 4,677,676.

Still referring to FIG. 4, the reference signal x(k) inputs a copy 96 of the A filter 88. The copy 96 of the A filter 88 outputs a signal in line 98 to summer 100. A copy 102 of the recursive B filter 90 receives the correction signal y(k) as model input, and outputs a signal in line 104 that is summed with the signal in line 98 in summer 100 to yield the correction signal y(k).

The A filter model 88 inputs the filtered reference signal from line 76 and outputs a signal in line 106 to summer 108. The summer 108 sums the signal in 106 and a signal from the B filter model 90 in line 110 to yield the model output signal in line 112. The recursive B filter model 90 inputs the model output in line 112. The model error signal in line 82 is multiplied by the model output signal in line 112 by multiplier 114 which provides an error input signal in 116 to adapt B filter model 90. The error signal in line 82 is also provided to multiplier 118 where it is multiplied by the filtered reference signal in line 76 to provide an error input signal in line 120 to adapt the A filter model 88. In other respects, the system in FIG. 4 is similar to the system in FIG. 3, and like reference numerals have been used where appropriate.

FIG. 5 shows an equation error feedback active acoustic attenuation system 2 implementing the invention. The system 2 in FIG. 5 is similar in many respects to the system 1 in FIG. 3 and like reference numerals were used where appropriate to facilitate understanding. The system 2 in FIG. 5 does not have an input sensor 22 like the system in FIG. 3, but rather uses the uncanceled equation error signal in line 70 as transmitted in lines 122 and 124 as the reference signal x(k). The signal in line 70, which is used as a reference signal in the system, is transmitted in line 72 to the reference signal filter 74 as in the system 1 in FIG. 3. The uncanceled equation error signal that is transmitted from summer 62 through line 70 and 122 is also transmitted through line 126 to the model error summer 80. In other respects, the system 2 in FIG. 5 is similar to the system 1 shown in FIG. 3.

FIG. 6 shows a feedforward, multiple input, multiple output (MIMO) system 3 implementing the invention. In general, a feedforward MIMO system 3 has a plurality of m input sensors represented by 22a and 22b, a plurality of n output transducers represented by 18a and 18b, and a plurality of p error sensors represented by 34a and 34b. The MIMO system 3 in FIG. 6 can be an m×n×p system but is shown as a 2×2×2 system for the sake of example. The MIMO system 3 in FIG. 6 is analogous to the single input single output (SISO) system in FIG. 3, and like reference numbers with corresponding a and b designations are used where appropriate to facilitate understanding.

Input sensor 22a senses the system input to generate a reference signal $x_1(k)$ in line 50a, and input sensor 22b senses the system input to generate a reference signal $x_2(k)$ in line 50b. The reference signals are input to model copy 52 which has a plurality of n×m channels. The model copy 52 is shown in FIG. 6 to be a direct FIR filter, however other filters such as an IIR filter can be used if desired. In FIG. 6, the model copy 52 has four channels: $A_{11}, A_{12}, A_{21},$ and $A_{22}$; and two summers: 123a and 123b (i.e. n=2). A correction signal $y_1(k)$ is output from summer 123a of the model copy 52 through line 56a. Likewise, a correction signal $y_2(k)$ is output from summer 123b of model copy 52 in line 56b. The correction signal $y_1(k)$ is transmitted in line 58a to drive output transducer 18a, and is also transmitted through line 64a to C model copy 66. Correction signal $y_2(k)$ is transmitted in line 58b to drive output transducer 18b, and also through line 64b to C model copy 66. C model 66 has four channels (i.e. p×n), and two summers 124a and 124b (i.e. p=2). An error sensor 34a senses the system output and generates an error signal $e_1(k)$ in line 60a. An error sensor 34b senses the system output and generates an error signal $e_2(k)$ in line 60b. Uncanceled equation error summer 62a sums the error signal. $e_1(k)$ in line 60a with the output from the C model copy 66 in line 68a to yield an uncanceled equation error signal in line 70a. Uncanceled equation error summer 62b sums the error signal $e_2(k)$ in line 60b with the filtered correction signal in line 68b to yield an uncanceled equation error signal in line 70b. FIG. 6 shows two (2) uncanceled equation error signals, but in general the number of equation error signals should equal the number of error sensors generating error signals.

A model output signal $my_1$ in line 78a is subtracted from the uncanceled equation error signal in line 70a in summer 80a to yield a model error signal $me_1$ in line 82a. A model output signal $my_2$ in line 78b is subtracted from the uncanceled equation error signal in line 70b in summer 80b to yield model error signal $me_2$ in line 82b. The model error signals $me_1$ and $me_2$ are used to adapt the adaptive channels in the model 54.

Reference signal $x_1(k)$ is also transmitted to a reference signal filter 74a through line 72a where it is processed through four (i.e. p×n) channels of a C model copy. The reference signal $x_1(k)$ in line 72a is processed through each channel of the C model copy 74a separately to generate four (i.e. p×n) filtered reference signals, $r_{111}, r_{121}, r_{211},$ and $r_{221}$. The filtered reference signal $r_{111}$ is input to the adaptive filter model channel $A_{11}$ to generate an element output signal that is transmitted to summer 130a. Filtered reference signal $r_{121}$ is processed through adaptive filter model channel $A_{21}$ to generate an element output signal that is transmitted to summer 130a. Filtered reference signal $r_{211}$ is processed through adaptive filter model channel $A_{11}$ to generate an element output signal that is transmitted to summer 130b. Filtered reference signal $r_{221}$ is processed through adaptive filter channel $A_{21}$ to generate an element output signal that is transmitted to 130b.

In a similar fashion, reference signal $x_2(k)$ is transmitted through line 72b to a reference signal filter 74b, and is processed through each separate channel of C model copy to generate filtered reference signals $r_{112}, r_{122}, r_{212},$ and $r_{222}$. The filtered reference signal $r_{112}$ is processed through adaptive filter model channel $A_{12}$ to generate an element output signal that is transmitted to summer 130a. A filtered reference signal $r_{122}$ is processed by adaptive filter model channel $A_{22}$ to generate an element output signal that is transmitted to summer 130a. The filtered reference signal $r_{212}$ is processed through adaptive filter model channel $A_{12}$ to generate an element output signal that is transmitted to summer 130b. The filtered reference signal $r_{222}$ is processed through adaptive filter model channel $A_{22}$ to generate an element output signal that is transmitted to summer 130b. The summer 130a outputs model output signal $my_1$ in line 78a. The summer 130b outputs model output signal $my_2$ in line 78b. FIG. 6 shows two model output summers, 130a and 130b, but in general there are a plurality of p model output summers.

Each adaptive filter model channel $A_{ij}$ is adapted using each of the p model error signals $me_1$ and $me_2$ (i.e. p=2 in FIG. 6). For instance, the preferred method of adapting for the adaptive filter model channels $A_{11}$, $A_{21}$, $A_{12}$, and $A_{22}$ can be represented by the following equations:

$$A_{11}: (r_{111} \otimes me_1) + (r_{211} \otimes me_2) \quad (1)$$

$$A_{12}: (r_{112} \otimes me_1) + (r_{212} \otimes me_2) \quad (2)$$

$$A_{21}: (r_{121} \otimes me_1) + (r_{221} \otimes me_2) \quad (3)$$

$$A_{22}: (r_{122} \otimes me_1) + (r_{222} \otimes me_2) \quad (4)$$

Where the symbol $\otimes$ represents a multiplier for correlating a regressor (i.e. $r_{ijk}$) and a model error signal (i.e. $me_i$) in an LMS update. In general, there are n×m adaptive filter model channels $A_{ij}$, and each is updated using each of the p model error signals.

FIG. 7 shows a feedback MIMO system 4. The system 4 in FIG. 7 is similar in many respects to the system 3 in FIG. 6, and like reference numbers are used where appropriate. Like the SISO feedback system 2 shown in FIG. 5, the MIMO system 4 in FIG. 7 uses the uncanceled equation error signals in lines 70a and 70b as model input signals in lines 72a and 72b. In addition, uncanceled equation error signal in line 70a is transmitted through lines 122a and 124a to be used as a reference signal to the model copy 52. Likewise, the uncanceled equation error signal in line 70b is transmitted through lines 122b and 124b to be used as a reference signal to the model copy 52. The uncanceled equation error signals in lines 70a and 70b are also transmitted through lines 122a and 122b and through lines 126a and 126b, to the model error summers 80a and 80b. In this system, the number of reference signals equals the number of error sensors. In other respects, the system 4 in FIG. 7 can be implemented similar to the system 3 in FIG. 6.

It is recognized that various equivalents, alternatives and modifications are possible within the scope of the appended claims. For instance, while this preferred embodiment shows the invention implemented in an active sound attenuation system, the invention as disclosed, can be used in other active control applications.

I claim:

1. An adaptive controller comprising:
   an IIR adaptive filter model with an error input that depends on a model error signal which is a combination of an error signal from an error sensor, a filtered correction signal which is generated by filtering a correction signal used to create a secondary input that combines with a system input to yield a system output, and a model output signal from the adaptive IIR filter model.

2. In an adaptive control system having an output transducer that receives a correction signal from an adaptive controller and outputs a control signal that combines with a system input to yield a system output, and an error sensor that senses the system output and outputs an error signal to the adaptive controller, an improvement in the adaptive controller comprising:

a correction signal filter that receives the correction signal and outputs a filtered correction signal;

an uncancelled equation error summer that receives the error signal and the filtered correction signal and outputs an uncancelled equation error signal;

a reference signal filter that receives a reference signal and outputs a filtered reference signal;

an adaptive filter model that receives the filtered reference signal and outputs a model output signal;

a model error summer that receives the uncancelled equation error signal and the model output signal, and outputs a model error signal that is used to adapt the adaptive filter model;

a copy of the adaptive filter model that receives the reference signal and outputs the correction signal;

an input sensor that senses the system input and outputs an input signal to the adaptive controller;

an adaptive D filter model that receives the correction signal and outputs a D model output signal; and a reference signal summer that receives the input signal from the input sensor and the D model output signal and outputs the reference signal.

3. In an adaptive control system having an output transducer that receives a correction signal from an adaptive controller and outputs a control signal that combines with a system input to yield a system output, and an error sensor that senses the system output and outputs an error signal to the adaptive controller, an improvement in the adaptive controller comprising:

a correction signal filter that receives the correction signal and outputs a filtered correction signal;

an uncancelled equation error summer that receives the error signal and the filtered correction signal and outputs an uncancelled equation error signal;

a reference signal filter that receives a reference signal and outputs a filtered reference signal;

an adaptive filter model that receives the filtered reference signal and outputs a model output signal;

a model error summer that receives the uncancelled equation error signal and the model output signal, and outputs a model error signal that is used to adapt the adaptive filter model; and a copy of the adaptive filter model that receives the reference signal and outputs the correction signal;

wherein the uncancelled equation error signal is also used as the reference signal.

4. In an adaptive control system having an output transducer that receives a correction signal from an adaptive controller and outputs a control signal that combines with a system input to yield a system output, and an error sensor that senses the system output and outputs an error signal to the adaptive controller, an improvement in the adaptive controller comprising:

a correction signal filter that receives the correction signal and outputs a filtered correction signal;

an uncancelled equation error summer that receives the error signal and the filtered correction signal and outputs an uncancelled equation error signal;

a reference signal filter that receives a reference signal and outputs a filtered reference signal;

an adaptive filter model that receives the filtered reference signal and outputs a model output signal;

a model error summer that receives the uncancelled equation error signal and the model output signal, and outputs a model error signal that is used to adapt the adaptive filter model; and a copy of the adaptive filter model that receives the reference signal and outputs the correction signal;

wherein the adaptive filter model is an IIR filter.

5. An adaptive control system having a system input and a system output, the system comprising:

a plurality of n output transducers each receiving one of n correction signals and outputting a secondary input that combines with the system input to yield the system output;

a correction signal filter having p×n channels, the correction signal filter receiving n correction signals and outputting p filtered correction signals;

a plurality of p error sensors, each error sensor sensing the system output and outputting an error signal;

a plurality of p uncancelled equation error summers, each uncancelled equation error summer receiving one of the p error signals and one of the p filter correction signals and outputting an uncancelled equation error signal;

an adaptive filter model having p adaptive elements corresponding to each of n×m filter model channels, each of the p×n×m adaptive elements outputting an element output signal;

a reference signal filter corresponding to each adaptive filter model element, each reference signal filter receiving one of m reference signals and outputting a filtered reference signal to the corresponding adaptive filter model element;

a plurality of p model output summers, each summing n×m element output signals to yield p model output signals for each model output summer;

a plurality of p model error summers, each receiving an uncancelled equation error signal from one of the uncancelled equation error summers and a model output signal from one of the model output summers, and outputting one of p model error signals wherein each model error signal is used to update each of the n×m channels in the adaptive filter model; and a copy of the adaptive filter model that receives the m reference signals and outputs the n correction signals.

6. The system as recited in claim 5 further comprising a plurality of m input sensors, each sensing the system input and outputting an input signal that is used as one of the m reference signals.

7. The system as recited in claim 5 further comprising:

a plurality of m input sensors each sensing the system input and outputting an input signal;

an adaptive D filter model that receives the n correction signals and outputs a plurality of m D Model output signals; and a plurality of m reference signal summers each receiving an input signal and a D model output signal and outputting one of the m reference signals.

8. A system as recited in claim 5 wherein the p uncancelled equation error signals are also used as the m reference signals.

9. A system as recited in claim 5 wherein the adaptive control system is an active acoustic attenuation system, the system input is an input acoustic wave, and the system output is an output acoustic wave.

10. A system as recited in claim 9 wherein the active acoustic attenuation system is a sound attenuation system, the output transducers are loudspeakers, and the error sensors are microphones.

11. A system as recited in claim 9 wherein the active acoustic attenuation system is a vibration control system, the output transducers are shakers, and the error sensors are accelerometers.

12. An adaptive control method in an active control system having a system input and a system output comprising the steps of:

generating a control signal from a correction signal;

combining the control signal with the system input to yield the system output;

sensing the system output and generating an error signal in response thereto;

filtering the correction signal to yield a filtered correction signal;

combining the filtered correction signal and the error signal to yield an uncancelled equation error signal;

filtering a reference signal to yield a filtered reference signal;

processing the filtered reference signal through an adaptive filter model to generate a model output signal;

combining the uncancelled equation error signal and the model output signal to yield a model error signal;

adapting the adaptive filter model at least in part in response to the model error signal;

processing the reference signal through a copy of the adaptive filter model to generate the correction signal;

sensing the system input and generating an input signal in response thereto;

processing the correction signal through a D model to generate a D model output signal; and combining the D model output signal and the input signal to generate the reference signal.

13. An adaptive control method in an active control system having a system input and a system output comprising the steps of:

generating a plurality of n control signals, each from one of n correction signals; signal;

combining the control signals with the system input to yield the system output;

sensing the system output and generating a plurality of p error signals in response thereto;

processing the n correction signals through a copy of a p×n C model to generate p filtered correction signals;

combining the p error signals and the p correction signals to yield p uncancelled equation error signals;

separately processing each of a plurality of m reference signals through each of p×n channels of a copy of the C model to generate m×p×n filtered reference signals;

processing the filtered reference signals through an adaptive filter model to generate a plurality of p model output signals;

combining the p uncancelled equation error signals and the p model output signals to generate p model error signals;

using the p model error signals to adapt the adaptive filter model; and processing the m reference signals through a copy of the adaptive filter model to generate the n correction signals.

* * * * *